US005775339A

United States Patent [19]
Woodburn et al.

[11] Patent Number: 5,775,339
[45] Date of Patent: Jul. 7, 1998

[54] PHOTODYNAMIC THERAPY OF PIGMENT-RELATED LESIONS

[75] Inventors: Kathryn W. Woodburn; Qing Fan, both of Sunnyvale; Stuart W. Young, Portola Valley, all of Calif.

[73] Assignee: Pharmacyclics, Inc., Sunnyvale, Calif.

[21] Appl. No.: 914,272

[22] Filed: Aug. 19, 1997

Related U.S. Application Data

[63] Continuation of Ser. No. 624,311, Mar. 26, 1996, abandoned.

[51] Int. Cl.$^6$ .................................................. A61B 19/00
[52] U.S. Cl. ........................... 128/898; 607/88; 607/901
[58] Field of Search ............................ 128/898; 607/88, 607/901; 534/15, 11; 504/465, 472

[56] References Cited

U.S. PATENT DOCUMENTS

| | | |
|---|---|---|
| 4,935,498 | 6/1990 | Sessler et al. . |
| 5,252,720 | 10/1993 | Sessler et al. . |
| 5,457,183 | 10/1995 | Sessler et al. . |
| 5,576,013 | 11/1996 | Williams et al. . |

FOREIGN PATENT DOCUMENTS

| | | | |
|---|---|---|---|
| 90/10633 | 9/1991 | WIPO . | |
| 93/14093 | 7/1993 | WIPO . | |
| 94/23916 | 12/1994 | WIPO . | |
| 95/10307 | 4/1995 | WIPO . | |
| 95/21845 | 8/1995 | WIPO . | |
| WO 95/24930 | 9/1995 | WIPO . | |
| 96/09315 | 3/1996 | WIPO . | |
| WO97/35617 | 10/1997 | WIPO .................................. | 128/898 |

OTHER PUBLICATIONS

Baumal, et al., "Photodynamic Therapy (PDT) of Experimental Choroidal Neovascularization with Tin Ethyl Etiopurpurin," *Investigative Ophthalmology & Visual Science,* vol. 37, No. 3, Feb. 15, 1996.

Henderson, et al., "How does Photodynamic Therapy Work?" *Photochemistry and Photobiology,* vol. 55, No. 1, pp. 145–157, 1992.

Kliman, et al., "Phthalocyanine Photodynamic Therapy: New Strategy for Closure of Choroidal Neovascularization," *Lasers in Surgery and Medicine,* 15:2–10, 1994.

Kliman, et al., "Retinal and Choroidal Vessel Closure Using Phthalocyanine Photodynamic Therapy," *Lasers in Surgery and Medicine,* 15:11–18, 1994.

Levy, Julia G., "Photosensitizers in Photodynamic Therapy," *Seminars in Oncology,* vol. 21, No. 6, Suppl. 15 (Dec.), pp. 4–10, 1994.

Miller, et al., "Phthalocyanine Photodynamic Therapy of Experimental Iris Neovascularization," *Ophthalmology,* vol. 98, No. 11, pp. 1711–1719, Nov. 1991.

Morgan, et al., "Tin (IV) Etiopurpurin dichloride: An Alternative to DHE?" *SPIE vol. 847 New Directions in Photodynamic Therapy,* pp. 172–179, 1987.

Young, et al., "Lutetium Texaphyrin (PCI–0123): A Near–Infrared Water–Soluble Photosensitizer," *Photochemistry and Photobiology,* 63(6), pp. 892–897, 1996.

Andreoni, et al., "B16 melanoma response in vivo to photochemotherapy with mitoxantrone and red light," *Cancer Letters,* 61, pp. 89–94, 1991.

Sessler et al., "Texaphyrins: Synthesis and Applications," *Accounts of Chemical Research,* 27(2):43–50, 1994.

Leff, "Texas 'Son–of–Porphyrin' Molecule Lassos Europium to Kill Drug Resistance Gene," *BioWorld Today,* 5(156):1, 1994.

Young et al., "Preclinical Evaluation of Gadolinium (III) Texaphyrin Complex. A New Paramagnetic Contrast Agent for Magnetic Resonance Imaging," *Investigative Radiology,* 29(3):330–338, 1994.

Furuta et al., "Enhanced Transport of Nucleosides and Nucleoside Analogues with Complementary Base–Pairing Agents," *Journal of the American Chemical Society,* 113:4706–4707, 1991.

Sessler et al., "Anion Binding: A New Direction In Porphyrin–Related Research," *Pure & Applied Chem.,* 65(3):393–398, 1993.

Sessler et al., "Synthesis and Binding Properties of Monomeric and Dimeric Guanine and Cytosine Amine Derivatives," *J. Org. Chem.,* 1992, 57:818–826.

T.D. Mody et al., "Lutetium (III) Texaphyrin: A Novel Photodynamic Therapy Agent," Abstract, *22nd Annual American Society for Photobiology,* Scottsdale, AZ, Jun. 25–29, 1994.

Sessler et al., "Gadolinium (III) Texaphyrin: A Novel MRI Contrast Agent," *Journal of the American Chemical Society,* 115(22):10368–10369, 1993.

Iverson et al., "Interactions Between Expanded Porphyrins and Nucleic Acids," *Pure Applied Chemistry,* 66(4):845–850, 1994.

Magda et al., "Site–Specific Hydrolysis of RNA by Europium (III) Texaphyrin Conjugated to a Syntheitc Oligodeoxyribonucleotide," *Journal of the American Chemical Society,* 116(16):7439–7440, 1994.

Koenig et al., "PDT of Tumor–Bearing Mice Using Liposome Delivered Texaphyrins," International Conference, Milan, Italy, Biosis citation only, Jun. 24–27, 1992.

(List continued on next page.)

*Primary Examiner*—Aaron J. Lewis
*Assistant Examiner*—Kelly O'Hara
*Attorney, Agent, or Firm*—Akin, Gump, Strauss, Hauer & Feld, L.L.P.

[57] ABSTRACT

The present invention involves the use of a photosensitive texaphyrin for the photodynamic treatment of a pigmented lesion, such as a melanodermic lesion, or a lesion obscured by pigmented tissue such as melaniferous tissue in a subject. In particular, the invention provides a treatment for the metastatic process of melanoma, and a method for inhibiting growth of established metastases of melanoma. The photosensitive texaphyrin may be a free-base texaphyrin or may be metallated with a diamagnetic metal. Preferably, the texaphyrin is metallated with lutetium. Heretofore, melanoma has been refractory to treatment with photodynamic therapy.

26 Claims, No Drawings

Mastruzzo et al., "Targeted Photochemical Modification of HIV–Derived Oligoribonucleotides by Antisense Oligodeoxynucleotides Linked to Porphyrins,"*Photochemistry and Photobiology*, vol. 60, No. 4, pp. 316–322, 1994.

Dougherty, "Photosensitizers: Therapy and Detection of Malignant Tumors", *Photochem. Photobiol.*, 45:879–889, (1987).

Magda et al., "Sequence–Specific Photocleavage of DNA by an Expanded Porphyrin with Irradiation Above 700nm," *J. Am. Chem. Soc.*, 117:3629–3630, 1995.

Sessler et al., "Expanded Porphyrins. Receptors for Cationic, Anionic, and Neutral Substrates," in Transition Metals in Supramolecular Chemistry, L. Fabbrizzi and A. Poggi, Editors, NATO ASI Series, Kluwer, Amsterdam, pp. 391–408, 1994.

PCT Search Report mailed Feb. 23, 1995.

International Search Report mailed Dec. 6, 1994.

International Search Report mailed Feb. 22, 1994.

International Search Report mailed Feb. 3, 1994.

Ehrenberg et al., "Spectroscopy, Photokinetics and Cellular Effect of Far–Red and Near Infrared Absorbing Photosensitizers," *Proc. SPIE–Int. Soc. Opt. Eng 1992, 1645 (Proc. Opt. Methods Tumor Treat. Dect.: Mech. Tech. Photodyn. Ther ...*, 259–263, 1992.

Thaller et al., "Potential Use of Radiolabelled Porphyrins for Tumor Scanning," *Porphyrin Photosensitization*, Kessel and Dougherty, Eds., Plenum Press, New York and London, Pubisher, pp. 265–278, 1981.

[edited by] DeVita, et al. *Cancer:Principles & Practice of Oncology*; 4th Edition; published by J.B. Lippincott Company, Philadelphia, pp. 2661–2666 and p. 19 of the index, 1993.

Brown and Truscott, "New Light on Cancer Therapy," *Chemistry in Britain*, 955–958, 1993.

Ehrenberg et al., "The Binding and Photosensitization Effects of Tetrabenzoporphyrins and Texaphyrin in Bacterial Cells," *Lasers in Medical Science*, 8:197–203, 1993.

Morgan and Skalkos, "Second Generation Sensitizers: Where are We and Where Should We Be Going?" *Proc. SPIE Int. Soc. Opt. Eng. Ser.*, 6:87–106, 1990.

Horstman, "Study to examine skin cancer drug activated by light," *Stanford University Campus Report*, Mar. 1996.

Biolo, et al., "Photodynamic Therapy of B16 Pigmented Melanoma With Liposome–Delivered Si(IV)–Naphthalocyanine," *Photochemistry and Photobiology*, vol. 59, No. 3, pp. 362–265, 1994.

Haylett, et al., "Pharmacokinetic and therapeutic outcome in melanoma cells, of the administration of symmetric and asymmetric cationic photosensitizers," *Cancer Letters 88*, pp. 191–199, 1995.

Leunig, et al., "Tumour localisation kinetics of photofrin and three synthetic porphyrinoids in an amelanotic melanoma of the hamster," *Br. J. Cancer*, 68, pp. 225–234, 1993.

Menon, et al., "Inhibition of lung metastasis in mice induced by B16F10 melanoma cells by polyphenolic compounds," *Cancer Letters 95*, pp. 221–225, 1995.

Nannmark, et al., "Microvessel Origin and Distribution in Pulmonary Metastases of B16 Melanoma: Implication for Adoptive Immunotherapy," *Cancer Research 55*, pp. 4627–4632, Oct. 15, 1995.

Nelson, et al., "Photodynamic Therapy of Human Malignant Melanoma Xenografts in Athymic Nude Mice," *Journal of the National Cancer Institute*, vol. 80, No. 1, Mar. 2, 1988.

Sealy, et al., "Photosensitization of Melanin: An Electron Spin Resonance Study of Sensitized Radical Production and Oxygen Consumption," *Photochemistry and Photobiology*, vol. 40, No. 4, pp. 453–459, 1984.

"Skin Cancer," *Canstat*, No. 20, pp. 1–15, Mar. 1995.

Dialog Search, 1996.

Search, 1996.

PCT/US90/01208 Int'l Search Report mailed Aug. 2, 1990.

PCT/US95/12312 International Search Report mailed Feb. 9, 1996.

König et al., "PDT of Tumor–Bearing Mice Using Liposome Delivered Texaphyrins", International Conference on Photodynamic Therapy and Medical Laser Applications, Milan, Italy, Photodynamic Therapy and Biomedical Lasers, ed. Spinelli et al., Elsevier Science Publishers B.V., pp. 802–805, 1992.

König et al., "Photodynamic Activity of Liposome–Delivered Cd–Texaphyrin Using Tumor–Bearing Nude Mice", *Lasers in Surgery and Medicine* 13:522–527, 1993.

U.S. Serial No. 08/196,964 to Sessler et al. filed Feb. 15, 1994.

U.S. Serial No. 08/227,370 to Sessler et al. filed Apr. 14, 1994.

U.S. Serial No. 08/207,845 to Sessler et al. filed Mar. 8, 1994.

U.S. Serial No. 08/236,218 to Sessler et al. filed Apr. 28, 1994.

U.S. Serial No. 08/310,501 to Sessler et al. filed Sep. 21, 1994.

U.S. Serial No. 08/433,573 to Sessler et al. filed May 3, 1995.

U.S. Serial No. 08/484,551 to Sessler et al. filed Jun. 7, 1995.

U.S. Serial No. 08/458,347 to Sessler et al. filed Jun. 2, 1995.

U.S. Serial No. 08/459,333 to Sessler et al. filed Jun. 2, 1995.

U.S. Serial No. 08/485,581 to Magda et al. filed Jun. 7, 1995.

U.S. Serial No. 08/469,177 to Magda et al. filed Jun. 6, 1995.

U.S. Serial No. 08/486,311 to Magda et al. filed Jun. 7, 1995.

U.S. Serial No. 08/487,722 to Magda et al. filed Jun. 7, 1995.

U.S. Serial No. 08/591,318 to Young et al. filed Jan. 25, 1996.

Sessler et al., "Synthesis and Crystal Structure of a Novel Tripyrrane–Containing Porphyrinogen–like Macrocycle", *J. Org. Chem.*, 52:4394–4397, 1987.

Sessler et al., "The Coordination Chemistry of Planar Pentadentate Porphyrin–Like Ligands", *Comm. Inorg. Chem.*, 7:333–350, 1988.

Sessler et al., "An Expanded Porphyrin: The Synthesis and Structure of a New Aromatic Pentadentate Ligand", *J. Am. Chem. Soc.*, 110:5586–5588, 1988.

Sessler et al., "A Water–Stable Gadolinium (III) Complex Derived from a New Pentadentate Expanded Porphyrin Ligand", *Inorg. Chem.*, 28:3390–3393, 1989.

Sessler et al., "Binding of Pyridine and Benzimidazole to a Cadmium Expanded Porphyrin: Solution and X–ray Structural Studies", *Inorg. Chem.*, 28:1333–1341, 1989.

Harriman et al., "Metallotexaphyrins: A New Family of Photosensitisers for Efficient Generation of Singlet Oxygen", *J. Chem. Soc., Chem. Commun.*, 314–316, 1989.

Sessler et al., "Expanded Porphyrins: The Synthesis and Metal Binding Properties of Novel Tripyrrane–Containing Macrocylces", *J. Coord. Chem.*, 18:99–104, 1988.

Sessler et al., "The Synthesis and Structure of a Novel 22 – Electron Aromatic Pentadentate Macrocyclic Ligand: An Expanded Porphyrin", Toronto ACS Meeting, Jun. 1988, USA.

Sessler et al., "A Water–Stable Gadolium (III) Complex Derived from a New Pentadentate Expanded Porphyrin Ligand", *Chem. Absts.*, 111:720, abstract No. 125716e, Oct. 2, 1989.

Stinson, "Unusual Porphyrin Analog Promises Many Applications", *Chemical and Engineering News*, pp. 26–27, Aug. 8, 1988.

Sessler et al., "Tripyrroledimethine–derived (Texaphyrin–type) Macrocycles: Potential Photosensitizers Which Absorb in the Far–red Spectral Region", *SPIE, Optical Methods for Tumor Treatment and Early Diagnosis: Mechanisms and Technique*, 1426:318–329, 1991.

Sessler et al., "'Texaphyrin': A Novel 22 –Electron Aromatic Pentadentate Macrocyclic Ligand", *ACS Meeting*, Los Angeles, Sep. 1988.

Sessler and Burrell, "Expanded Porphyrins," *Topics in Current Chemistry*, 161:180–273, 1991.

Sessler et al., "Synthesis and Structural Characterization of Lanthanide(III) Texaphyrins," *Inorganic Chemistry*, 32(14):3175–3187, 1993.

Sessler et al., "Preparation of Lanthanide (III) Texaphyrin Complexes and Their Applications to Magnetic Resonance Imaging and Photodynamic Therapy," *Abstracts of Papers*, Part 1, 204th ACS National Meeting, Aug. 23–28, 1992, Washington, DC.

Sessler et al., "Synthesis and Applications of Schiff–Base Derived Expanded Porphyrins," *Abstracts of Papers*, Part 1, 204th ACS National Meeting, Aug. 23–28, Washington, DC.

Sessler, Jonathan L., "Texas–Sized Molecule," *Discovery*, 13(1):44–49, 1993.

Sessler et al., "Photodynamic Inactivation of Enveloped Viruses Using Sapphyrin, 22 –Electron Expanded Porphyrin: Possible Approaches to Prophylactic Blood Purification Protocols," *SPIE Photodynamic Therapy: Mechanisms II*. 1203:233–245, 1990.

Maiya et al., "Ground–and Excited–State Spectral and Redox properties of Cadmium(II) Texaphyrin," *Journal of Physical Chemistry*, 93(24):8111–8115, 1989.

PCT Search Report mailed Jul. 21, 1997.

Woodburn, et al., "Biological Analysis of Lutetium Texaphyrin," *Abstracts of the 24th Annual Meeting of the American Society for Photobiology*, p. 80S, Jun. 1996.

Dialog File Supplier: File 187: F–D–C Reports; The Pink Sheet, vol. 58, No. 27, "Pharmacyclics Gd–Tex for brain metastases in Phase I/II multicenter trial," Jul. 1, 1996.

Dialog File Supplier: File 187: F–D–C Reports; Pharmaceutical Approvals Monthly, vol. 1, No. 7, "Clinical Trial Updates: Company–Sponsored Studies: Pharmacyclics," Jul. 1, 1996.

Dialog File Supplier: File 129: PHIND AN=00414390, "Pharmacyclics' Gadolite to enter Phase III clinical trials," Aug. 30, 1994.

PHOTODYNAMIC THERAPY OF PIGMENT-RELATED LESIONS

This application is a continuation application of Ser. No. 08/624,311, filed Mar. 26, 1996, now abandoned.

FIELD OF THE INVENTION

The present invention relates generally to the fields of dermatology and oncology, and to methods for treating pigment-related lesions, i.e., lesions containing pigment or lesions covered by or adjacent to pigmented tissue. More particularly, it concerns the use of a photosensitive texaphyrin in photodynamic therapy of melanodermic or other pigmented lesions, and lesions obscured by melaniferous or other pigmented tissue of a subject. In particular, methods are provided for the treatment of melanoma, and inhibition of metastasis of melanoma.

BACKGROUND OF THE INVENTION

Melanins are pigments responsible for the dark color of skin, hair, feathers, fur, insect cuticle, the choroid coat of the eye, and the substantia nigra of the brain. Melanins are also found in fungi, bacteria, and pathological human urine where they can be an indication of melanotic tumors. These pigments are synthesized into the skin by melanocytes; they have a broad absorption spectrum from 250 nm–1,200 nm and are sometimes referred to as providing a "light absorbing mantle." Eumelanins (sepiomelanin, melanoma-melanin) and phaeomelanins are found in the animal kingdom, the latter group being lighter in color. The chemical units that predominate in these melanins are indole-related, formed from tyrosine and dopa precursors.

Without melanin pigmentation of the skin, humans could not tolerate exposure to the sun without fear of excessive sunburn. Malignant melanomas arise from melanocytes and can be pigmented (melanotic) due to accumulation of melanin, which imparts a dark color to these lesions. Due to the fact that some melanocytes may be less well-differentiated and therefore produce less melanin, these malignant lesions may also be nonpigmented or amelanotic.

Hyperpigmentation usually reflects increased melanization of the epidermis. Differences in melanosome formation and distribution account for normal variations in pigmentation. Stimulation of melanocytes in blacks and certain other races results in production of large melanosomes that are dispersed individually within keratinocytes throughout the epidermis. In fair-skinned people, smaller melanosomes aggregate mainly in the lower epidermal layer. Localized hyperpigmentation include ephelides (freckles), solar or senile lentigines (liver spots), mongolian spots, cafe au lait spots, and melasma which is common during pregnancy. Acanthosis nigricans is a hypermelanotic disorder that produces brownish, verrucous, papillomatous changes of the epidermis.

Of the skin cancers, melanoma causes the largest number of deaths. Because it may act as a cocarcinogen or promoter, solar radiation may be related to the onset of melanoma. This hypothesis is supported by the fact that the highest rates of malignant melanoma are in fair-skinned populations who are exposed by habitation or recreational habits to sunny climates, and that melanoma has a predilection for areas of the body exposed to sunlight during recreational activities. Dysplastic nevi are the major precursor lesions of melanoma and show variegated pigmentation.

Photodynamic therapy (PDT) is a treatment technique that uses a photosensitizing dye that produces cytotoxic materials, such as singlet oxygen ($O_2(^1\Delta_g)$) from benign precursors (e.g. ($O_2(^3\Sigma_g^-)$), when irradiated in the presence of oxygen. Other reactive species such as superoxide, hydroperoxyl, or hydroxyl radicals may be involved. At the doses used, neither the light nor the drug has any independent activity against the disease target.

The effectiveness of PDT is predicated on three additional factors: i) The photosensitive dyes used in PDT preferably have the ability to localize at the treatment site as opposed to surrounding tissue. ii) The high reactivity and short lifetime of activated oxygen means that it has a very short range and is unlikely to escape from the cell in which it is produced; cytotoxicity is therefore restricted to the precise region of photoactivated drug. iii) Developments in light delivery, such as lasers, light emitting diodes, and fiber optics, allow a beam of intense light to be delivered accurately to many parts of the body.

For reviews of photodynamic therapy, see U.S. Pat. No. 5,252,720 (incorporated by reference herein); Sindelar et al., (1991); Grossweiner, L. I., (1991); Henderson, B. W. and T. J. Dougherty, (1992); and Moan, J. and K. Berg, (1992). In recent years, considerable effort has been devoted to the synthesis and study of new photosensitizers (a review is found in Brown, S. B. and Truscott, T. G., 1993). The development of more effective photochemotherapeutic agents requires the synthesis of compounds which absorb in the spectral region where living tissues are relatively transparent (i.e., 700–1000 nm), have high triplet quantum yields, are minimally toxic, and have physiologically acceptable water/lipid partition coefficients.

PDT has been successfully used for the treatment of cutaneous and subcutaneous tumors (Dougherty, 1981). However, pigmented melanomas have been unresponsive, possibly due to poor light penetration into melanin-rich tissues (Pass, 1993), or due to the alleged ability of melanin to reduce singlet oxygen yields (Bielec et al., 1986; Sealy et al., 1984) and to scavenge free radical species; the latter ability also limits the efficacy of ionizing radiation (Haylett et al., 1995). PDT using hematoporphyrin derivative (HpD) has been successfully used in the treatment or retardation of lightly pigmented and amelanotic melanomas (Dougherty, 1981). However, the wavelength of light needed (630 nm) for this drug has only limited tissue penetration (MacRobert et al., 1989).

Silicon(IV)-naphthalocyanine is a longer wavelength absorbing photosensitizer with a strong absorption band at 776 nm (Biolo et al., 1994). This naphthalocyanine is highly hydrophobic and requires the use of liposomes for solubilization. However, silicon(IV)-naphthalocyanine displayed no tumor selectivity in a B16 murine melanoma model, and tumor retardation that was not associated with thermal effects was considered modest (Biolo et al., 1994). In studies performed with melanoma models, human xenograft melanotic tumors were not responsive to PDT with PHOTOFRIN® II (Nelson et al., 1988), despite containing more sensitizer than amelanotic melanoma. The lack of PDT response was credited to the inability of 630 nm light to penetrate the light shield provided by melanin. The effect of sensitizer and PDT on metastasis is an important consideration for the clinician. Localized PDT using PHOTOFRIN® II has been shown not to influence pulmonary metastases of Lewis Lung Carcinoma transplanted on the flanks of C57 mice (Gomer et al., 1987). Furthermore, PDT can induce immunosuppression due to activation of the complement system (Lim et al., 1985).

Texaphyrins are effective photosensitizers for use in PDT. They absorb strongly in the tissue-transparent 720–770 nm range, produce $^1O_2$ with an adequate quantum yield, and, since they are completely synthetic, can be modified so as to incorporate desired properties. Paramagnetic texaphyrins have exhibited significant tumor selectivity as detected by magnetic resonance imaging (Sessler et al., 1994; Young et al., 1994). Texaphyrin compounds and methods of preparation are described in U.S. Pat. Nos. 4,935,498, 5,162,509, 5,252,720, 5,272,142, 5,256,399, 5,292,414, 5,432,171, 5,439,570, 5,475,104, 5,451,576, 5,457,183, and 5,369,101; in pending applications Ser. Nos. 08/196,964, 08/227,370, 08/236,218, and 08/484,551; and in PCT publications WO 90/10633, WO 93/14093, and WO 94/29316; each patent, application, and publication is incorporated by reference herein.

Conventional PDT of melanotic melanoma has not been very successful; pigmented melanoma appears resistant to ionizing radiation, and disseminated melanoma is a very difficult tumor to treat, surgery being effective only when the tumor is localized. Therefore, new modes of treatment of pigmented lesions such as melanoma, or pigmented nevus, are of interest. The present invention addresses these problems in the art and provides methods effective for treating such lesions.

SUMMARY OF THE INVENTION

The present invention results from the discovery that a photoactivated texaphyrin is effective in photodynamic therapy of tissue containing pigment, such as melanin. That is, the effectiveness of photodynamic therapy with texaphyrins appears to persist even in the presence of pigmented tissue, such as melanin-containing tissue. Therefore, the present invention provides a method for photodynamic therapy of a pigmented lesion, such as a melanodermic lesion, or a lesion obscured by pigmented tissue, such as melaniferous tissue, of a subject. The method comprises administering a photosensitive texaphyrin to the subject and photoirradiating the lesion. In an aspect of the invention, the pigmented lesion may be a malignant lesion, a neoplasm, or other undesired pigmented cells and other tissues, such as hair-containing lesions, or hair. In a preferred embodiment, the malignant lesion is melanoma or other pigmented neoplasm.

The invention also provides a method for inhibiting the metastatic process, or the growth of established metastases of melanoma in a subject, comprising administering a photosensitive texaphyrin to the subject; and irradiating the subject.

The methods of the present invention may further comprise a step of determining localization sites of the photosensitive texaphyrin in the host by reference to the texaphyrin, or a step of administering ionizing or particulate radiation to the subject in proximity to a pigmented lesion or a lesion obscured by pigmented tissue.

Following long-standing patent law convention, the terms "a" and "an" mean "one or more" when used in this application, including the claims.

ABBREVIATIONS

FCS: fetal calf serum
HpD: hematoporphyrin derivative
MST: median survival time
PBS: phosphate buffered saline
PDT: photodynamic therapy

DETAILED DESCRIPTION OF THE PREFERRED EMBODIMENTS

The present invention provides for the use of a photosensitive texaphyrin in the photodynamic treatment of a pigmented lesion, such as a melanodermic lesion, or a lesion obscured by pigmented tissue, such as melaniferous tissue of a subject. In particular, the invention provides a treatment for melanoma, a method for inhibiting the metastatic process, and a method for inhibiting growth of established metastases of melanoma. Heretofore, melanoma has been refractory to treatment with photodynamic therapy.

By a "melanodermic lesion" is meant a lesion having an abnormal darkening of the skin by deposition of dark, brown, or black pigmentation; of excess melanin; of other substances that resemble melanin to varying degrees; or of metallic substances such as silver or iron. Hemochromatosis refers to lesions having iron deposition, for example. By "melaniferous" is meant containing melanin or other dark pigment. By "melanoma" is meant a malignant neoplasm derived from cells that are capable of forming melanin. By "melanin" is meant a dark brown to black polymer of indole 5,6-quinone and/or 5,6-dihydroxyindole 2-carboxylic acid that normally occurs in the skin, hair, or pigmented coat of the retina, for example.

By "a lesion obscured by pigmented tissue such as melaniferous tissue" is meant any lesion that may be a candidate for PDT including benign or malignant tumors, melanotic or amelanotic, where tissue containing melanin or other pigment is physically located in between a PDT light source and the lesion to be treated so as to hide, cover, or conceal the lesion to be treated. Since phototherapy with texaphyrins appears to persist even in the presence of pigmented tissue, light would pass through the pigmented tissue, and photoirradiate the tissue targeted for PDT.

By "melanotic" is meant pertaining to the normal or pathologic presence of melanin. By "amelanotic" is meant lacking melanin. The amelanotic lesion may be, but is not limited to, amelanotic melanoma. With the exception of in albino individual, people of all races have some melanin in their skin. An aspect of the invention that is particularly useful is the use of photosensitive texaphyrins in PDT for a subject having more than an average fair-skinned person amount of melanin in their skin. An example of a subject having an average fair-skinned person amount of melanin is an untanned Caucasian person. Examples of subjects having more than an average fair-skinned person amount of melanin include an American Indian, a Black person, a very tanned Caucasian person, an Hispanic person, an Asian person with dark pigmented skin, and the like.

Cancer occurs more often in the skin than at any other site. Primary malignant cutaneous tumors treatable by the present methods may arise from the epidermis, dermis, or subcutaneous tissue or from any of the specialized cell types in the skin or its appendages; malignant tumors that originate internally may eventually metastasize to the skin. Certain premalignant dermatoses that are described as cytologically malignant, yet biologically benign, may develop into malignant lesions and are considered treatable by methods of the present invention.

Malformations and tumors involving pigment-forming cells and treatable by the present invention include ephelis (freckle), hair, Becker's nevus, and lentigo from epidermal melanocytes; mongolian spot, blue nevus, cellular blue nevus from dermal melanocytes; congenital pigmented nevus, junctional nevus, compound nevus, intradermal nevus, and spindle cell nevus, basal cell nevus syndrome; venereal warts; and condyloma lata.

Several clinical types of melanoma have been recognized, all of which are expected to be treatable by PDT using photosensitive texaphyrins: acral lentiginous, amelanotic, benign juvenile, Cloudman, halo, Harding-Passey, malignant, malignant in situ, melanotic lentigo (Hutchinson freckle), minimal deviation, nodular, subungual, superficial spreading, desmoplastic, and neurotropic melanoma, for example.

Melanoma lesions may exhibit shades of tan, light to dark brown, and black caused by the presence of melanin-containing melanocytes at different levels of the epidermis. The lesions may also display blue, red, and white hues. The blue color is caused by the presence of melanin pigment in the deeper dermis, usually in melanophages; the red color reflects inflammation associated with dilated dermal blood vessels; and the white color is indicative of tumor regression with fibrosis. Melanomas usually metastasize first via the lymphatic system, with involvement of regional nodes, and then via blood vessels, with dissemination to subcutaneous tissue and to the liver, lungs, and brain.

Determining localization sites of a photosensitive texaphyrin is by reference to the texaphyrin. "By reference to the texaphyrin" as used herein means that the location may be found by localization such as magnetic resonance imaging if the texaphyrin contains a metal that is paramagnetic, gamma ray detection if the metal is gamma emitting, or by using monochromatic X-ray photon sources or fluorescent spectroscopy (see the U.S. Patents to texaphyrins cited herein, incorporated herein by reference for this purpose). A nonmetallated form of texaphyrin may be used, in particular, where fluorescence is the preferred means of detection of the texaphyrin. A texaphyrin having a methyl group attached to a ring nitrogen is described in related U.S. Pat. No. 5,457,183, incorporated by reference herein.

PDT using a texaphyrin may be carried out in combination with standard treatments, such as imaging, radiation, or hyperthermia, for example. Ionizing or particulate radiation may be administered to a subject in proximity to a pigmented lesion or a lesion obscured by pigmented tissue in addition to use of a photosensitive texaphyrin in PDT. Texaphyrins have been demonstrated to have radiation sensitization properties; they enhance cytotoxicity from ionizing radiation in the vicinity of the texaphyrin as compared to control experiments (see PCT publication WO 95/10307, incorporated by reference herein). Ionizing radiation includes, but is not limited to, x-rays, internal and external gamma emitting radioisotopes, and ionizing particles. Particulate radiation includes, but is not limited to, radiation with neutrons or electrons, for example, neutron capture. When photodynamic therapy and radiosensitization is carried out using a single texaphyrin, the texaphyrin is nonmetallated or metallated with a diamagnetic metal. When two different texaphyrins are used in a two-step process, the texaphyrin for PDT is nonmetallated or metallated with a diamagnetic metal, and the texaphyrin for radiosensitization is nonmetallated, or metallated with a diamagnetic or paramagnetic metal; the metal is not central to the radiosensitization properties of the texaphyrin.

An individual skilled in the art of organic synthesis in light of the present disclosure is able to prepare a large variety of photosensitive texaphyrins, all of which are expected to be effective in photodynamic therapy. The photosensitive texaphyrin may be a free-base texaphyrin or may be metallated with a diamagnetic metal. The term "photosensitive", as used herein, means that upon photoirradiation by light associated with the absorption profile of texaphyrin, texaphyrin effects the generation of oxygen products that are cytotoxic. Cytotoxic oxygen products may be singlet oxygen, hydroxyl radicals, superoxide, hydroperoxyl radicals, or the like. For generating singlet oxygen, the preferred metal is a diamagnetic metal. A preferred diamagnetic metal is Lu(III), La(III), In(III), Y(III), Dy(III), Zn(II), or Cd(II) and a most preferred diamagnetic metal is Lu(III).

In the present photodynamic therapy methods, the light source may be a laser or a light emitting diode, for example; the light may have a wavelength range of about 450–900 nm, preferably about 700–800 nm, more preferably about 730–770 nm; and the light may be administered topically, endoscopically, or interstitially (via, e.g., a fiber optic probe).

The photosensitive texaphyrin for use in treatment of a melanodermic lesion, or a lesion obscured by melaniferous tissue has structure A:

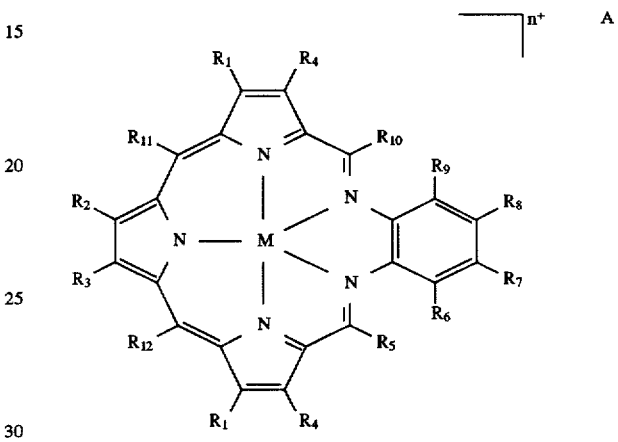

In this embodiment, M is H or a diamagnetic metal cation. $R_1$–$R_4$, $R_7$ and $R_8$ are independently hydrogen, halide, hydroxyl, alkyl, aryl, haloalkyl, nitro, formyl, acyl, hydroxyalkyl, alkoxy, hydroxyalkoxy, saccharide, carboxy, carboxyalkyl, carboxyamidealkyl, a site-directing molecule, or a couple that is coupled to a site-directing molecule.

$R_6$ and $R_9$ are independently selected from the groups of $R_1$–$R_4$, $R_7$ and $R_8$, with the proviso that the halide is other than iodide and the haloalkyl is other than iodoalkyl.

$R_5$ and $R_{10}$–$R_{12}$ are independently hydrogen, alkyl, aryl, hydroxyalkyl, alkoxy, hydroxyalkoxy, carboxyalkyl, carboxyamidealkyl or a couple that is coupled to a saccharide or to a site-directing molecule.

In one embodiment of the present invention, a texaphyrin is further coupled to a site-directing molecule to form a conjugate for targeted in vivo delivery. "Site-directing" means having specificity for targeted sites. "Specificity for targeted sites" means that upon contacting the texaphyrin-conjugate with the targeted site, for example, under physiological conditions of ionic strength, temperature, pH and the like, specific binding will occur. The interaction may occur due to specific electrostatic, hydrophobic, or other interaction of certain residues of the conjugate with specific residues of the target to form a stable complex under conditions effective to promote the interaction.

As used herein, a "site-directing molecule" may be an oligonucleotide, an antibody, a hormone, a peptide having affinity for a biological receptor, a sapphyrin molecule, or the like. A preferred site-directing molecule is a melanocyte-directed molecule, such as an antibody having binding specificity for a melanocyte-associated protein, for example, tyrosinase (an important enzyme in melanin synthesis), tyrosinase-related protein-1 (TRP-1, gp75), or gp100 (Chen et al., 1995). Monoclonal antibody T311 is an example of an antibody having binding specificity for tyrosinase (Chen et al., 1995), and antibody HMB45 is an example of an antibody having binding specificity for an epitope specific for melanocytes, malignant melanomas and melanoma metastases (Schwichheimer and Zhou, 1995). An exemplary oligonucleotide useful in antisense technology for targeting melanoma would be complementary to tyrosinase mRNA and capable of inhibiting translation, for example. The oligonucleotide may be complementary to a gene encoding tyrosinase, or regulatory regions thereof, so as to inhibit expression or replication, for example.

The texaphyrin may be a texaphyrin metal complex, and in this embodiment, the metal M is a diamagnetic metal cation and the diamagnetic metal cation preferably may be Lu(III), La(III), In(III), Y(III), Dy(III), Zn(II) or Cd(II).

The value, n, will typically be an integer less than or equal to 5. In the context of the basic macrocycle with a divalent or trivalent metal cation, n is 1 or 2; however, one skilled in the art in light of the present disclosure would realize that the value of n would be altered due to any charges present on substituents $R_1$–$R_{12}$. It is understood by those skilled in the art that texaphyrin metal complexes have one or more additional ligands providing charge neutralization and/or coordinative saturation to the metal ion. Such ligands include chloride, nitrate, acetate, and hydroxide, among others.

A couple may be described as a linker, i.e., the covalent product formed by reaction of a reactive group designed to attach covalently another molecule at a distance from the texaphyrin macrocycle. Exemplary linkers or couples are amides, amine, thiol, thioether, ether, or phosphate covalent bonds. In most preferred embodiments, site-directing molecules are covalently bonded to the texaphyrin via a carbon-nitrogen, carbon-sulfur, or a carbon-oxygen bond.

The following structure shows a correlation of the IUPAC nomenclature for the positions of the atoms around the periphery of the texaphyrin macrocycle with the positions of the R groups of the present invention.

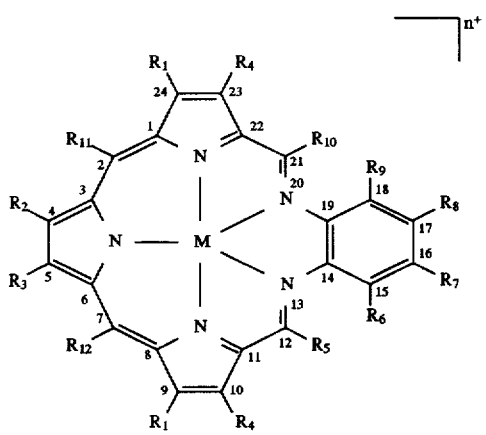

Substituents at the $R_6$ and $R_9$ positions on the B (benzene ring) portion of the macrocycle are incorporated into the macrocycle by their attachment to ortho-phenylenediamine in the 3 and 6 positions of the molecule. Substituents at the $R_5$ and $R_{10}$ positions on the T (tripyrrane) portion of the macrocycle are incorporated by appropriate functionalization of carboxyl groups in the 5 positions of the tripyrrane at a synthetic step prior to condensation with a substituted ortho-phenylenediamine.

In the texaphyrins of the present invention, the alkyl, aryl, hydroxyalkyl, oxyalkyl, oxyhydroxyalkyl, saccharide, carboxyalkyl, carboxyamidealkyl, site-directing molecule, or molecule couple is covalently bonded to the texaphyrin via a carbon-carbon, a carbon-nitrogen or a carbon-oxygen bond.

The aryl may be a compound whose molecules have the ring structure characteristic of benzene, naphthalene, phenanthrene, anthracene, and the like, i.e., either the 6-carbon ring of benzene or the condensed 6-carbon rings of the other aromatic derivatives. For example, an aryl group may be phenyl or naphthyl, unsubstituted or substituted with a nitro, carboxy, sulfonic acid, hydroxy, oxyalkyl or halide substituent. In this case, the substituent on the phenyl or naphthyl may be added in a synthetic step after the condensation step which forms the macrocycle.

Texaphyrins possess inherent biolocalization specificity for lipid-rich tissue, such as tumor, for example, as demonstrated in U.S. patents to texaphyrins cited herein and as demonstrated in Example 1. "Biolocalization specificity" means having an inherently greater affinity for certain tissues relative to surrounding tissues. Generally, water soluble texaphyrins retaining lipophilicity are preferred for the applications described herein. "Water soluble" means soluble in aqueous fluids to about 1 mM or better. "Retaining lipophilicity" means having greater affinity for lipid-rich tissues or materials than surrounding nonlipid-rich tissues or materials. "Lipid-rich" means having a greater amount of triglyceride, cholesterol, fatty acids or the like. Importantly, hydroxylated texaphyrins have a lipid-water distribution coefficient that is optimal for localization to lipophilic regions, yet sufficiently water soluble to allow ease of handling. Additional advantages of using texaphyrins for PDT include the strong absorption of light at wavelengths where tissue is more transparent, and the lack of toxicity of texaphyrins.

Representative examples of alkanes useful as alkyl group substituents of the present invention include methane, ethane, straight-chain, branched or cyclic isomers of propane, butane, pentane, hexane, heptane, octane, nonane and decane, with methane, ethane and propane being preferred. Representative examples of alkenes useful as alkenyl group substituents include ethene, straight-chain, branched or cyclic isomers of propene, butene, pentene, hexene, heptene, octene, nonene and decene, with ethene and propene being preferred. Representative examples of alkynes useful as alkynyl group substituents include ethyne, straight-chain, branched or cyclic isomers of propyne, butyne, pentyne, hexyne, heptyne, octyne, nonyne and decyne, with ethyne and propyne being preferred. Representative examples of substituted alkyls include alkyls substituted by two or more functional groups as described herein.

Among the halide substituents, chloride, bromide, fluoride and iodide are contemplated in the practice of this invention with the exception of iodide for $R_6$ and $R_9$. $R_6$ and $R_9$ may have chloride, bromide or fluoride substituents. Representative examples of haloalkyls used in this invention include halides of methane, ethane, propane, butane, pentane, hexane, heptane, octane, nonane and decane, with halides, preferably chlorides or bromides, of methane, ethane and propane being preferred.

Representative examples of hydroxyalkyls include alcohols of methane, ethane, straight-chain, branched or cyclic isomers of propane, butane, pentane, hexane, heptane, octane, nonane and decane, with alcohols of methane, ethane or propane being preferred. "Hydroxyalkyl" is meant to include glycols and polyglycols; diols of ethane, straight-chain, branched or cyclic isomers of propane, butane, pentane, hexane, heptane, octane, nonane and decane, with diols of ethane or propane being preferred; polyethylene glycol, polypropylene glycol and polybutylene glycol as well as polyalkylene glycols containing combinations of ethylene, propylene and butylene.

Representative examples of oxyalkyls include the alkyl groups as herein described having ether linkages. The number of repeating oxyalkyls within a substituent may be up to 100, preferably is from 1–10, and more preferably, is 2–5. A preferred oxyalkyl is $O(CH_2CH_2O)_xCH_3$ where $x=1$–100, preferably 1–10, and more preferably, 2–5.

Representative examples of thioalkyls include thiols of ethane, thiols of straight-chain, branched or cyclic isomers of propane, butane, pentane, hexane, heptane, octane, nonane and decane, with thiols of ethane (ethanethiol, $C_2H_5SH$) or propane (propanethiol, $C_3H_7SH$) being preferred. Sulfate-substituted alkyls include alkyls as described above substituted by one or more sulfate groups, a representative example of which is diethyl sulfate ($(C_2H_5)_2SO_4$).

Representative examples of phosphates include phosphate or polyphosphate groups. Representative examples of phosphate- substituted alkyls include alkyls as described above substituted by one or more phosphate or polyphosphate groups. Representative examples of phosphonate-substituted alkyls include alkyls as described above substituted by one or more phosphonate groups.

Representative examples of carboxy groups include carboxylic acids of the alkyls described above as well as aryl carboxylic acids such as benzoic acid. Representative examples of carboxyamides include primary carboxyamides ($CONH_2$), secondary ($CONHR'$) and tertiary ($CONR'R''$) carboxyamides where each of R' and R" is a functional group as described herein.

Representative examples of useful amines include a primary, secondary or tertiary amine of an alkyl as described hereinabove.

Exemplary site-directing molecules contemplated in the present invention include but are not limited to: polydeoxyribonucleotides, oligodeoxyribonucleotides, polyamides including peptides having affinity for a biological receptor and proteins such as antibodies; steroids and steroid derivatives; hormones such as estradiol, or histamine; hormone mimics such as morphine; and further macrocycles such as sapphyrins and rubyrins.

Representative examples of useful steroids include any of the steroid hormones of the following five categories: progestins (e.g. progesterone), glucocorticoids (e.g., cortisol), mineralocorticoids (e.g., aldosterone), androgens (e.g., testosterone) and estrogens (e.g., estradiol).

Representative examples of useful amino acids of peptides or polypeptides include amino acids with simple aliphatic side chains (e.g., glycine, alanine, valine, leucine, and isoleucine), amino acids with aromatic side chains (e.g., phenylalanine, tryptophan, tyrosine, and histidine), amino acids with oxygen and sulfur-containing side chains (e.g., serine, threonine, methionine, and cysteine), amino acids with side chains containing carboxylic acid or amide groups (e.g., aspartic acid, glutamic acid, asparagine, and glutamine), and amino acids with side chains containing strongly basic groups (e.g., lysine and arginine), and proline. Representative examples of useful peptides include any of both naturally occurring and synthetic di-, tri-, tetra-, pentapeptides or longer peptides derived from any of the above described amino acids (e.g., endorphin, enkephalin, epidermal growth factor, poly-L-lysine, or a hormone). Representative examples of useful polypeptides include both naturally occurring and synthetic polypeptides (e.g., insulin, ribonuclease, and endorphins) derived from the above described amino acids and peptides.

Hydroxyalkyl means alkyl groups having hydroxyl groups attached. Oxyalkyl means alkyl groups attached to an oxygen. Oxyhydroxyalkyl means alkyl groups having ether or ester linkages, hydroxyl groups, substituted hydroxyl groups, carboxyl groups, substituted carboxyl groups or the like. Saccharide includes oxidized, reduced or substituted saccharide; hexoses such as D-glucose, D-mannose or D-galactose; pentoses such as D-ribulose or D-fructose; disaccharides such as sucrose, lactose, or maltose; derivatives such as acetals, amines, and phosphorylated sugars; oligosaccharides, as well as open chain forms of various sugars, and the like. Examples of amine-derivatized sugars are galactosamine, glucosamine, sialic acid and D-glucamine derivatives such as 1-amino-1-deoxysorbitol. Carboxyamidealkyl means alkyl groups with hydroxyl groups, secondary or tertiary amide linkages or the like. Carboxyalkyl means alkyl groups having hydroxyl groups, carboxyl or amide substituted ethers, ester linkages, tertiary amide linkages removed from the ether or the like.

The term "a peptide having affinity for a biological receptor" means that upon contacting the peptide with the biological receptor, for example, under appropriate conditions of ionic strength, temperature, pH and the like, specific binding will occur. The interaction may occur due to specific electrostatic, hydrophobic, entropic or other interaction of certain amino acid or glycolytic residues of the peptide with specific amino acid or glycolytic residues of the receptor to form a stable complex under the conditions effective to promote the interaction. The interaction may alter the three-dimensional conformation and the function or activity of either or both the peptide and the receptor involved in the interaction. A peptide having affinity for a biological receptor may include an endorphin, an enkephalin, a growth factor, e.g. epidermal growth factor, poly-L-lysine, a hormone, a peptide region of a protein and the like. A hormone may be estradiol, for example.

In the practice of the present invention, preferred functionalizations for texaphyrin A are: when $R_6$ and $R_9$ are other than hydrogen, then $R_5$ and $R_{10}$ are hydrogen or methyl; and when $R_5$ and $R_{10}$ are other than hydrogen, then $R_6$ and $R_9$ are hydrogen, hydroxyl, or halide other than iodide. Other preferred functionalizations are where $R_6$ and $R_9$ are hydrogen, then $R_5$, $R_{10}$, $R_{11}$ and $R_{12}$ are lower alkyl or lower hydroxyalkyl. The lower alkyl is preferably methyl or ethyl, more preferably methyl. The lower hydroxyalkyl is preferably of 1 to 6 carbons and 1 to 4 hydroxy groups, more preferably 3-hydroxypropyl.

In a presently preferred texaphyrin A, $R_1$ is $(CH_2)_2CH_2OH$, $R_2$ and $R_3$ are $CH_2CH_3$, $R_4$ is $CH_3$, $R_8$ is a site-directing molecule or a couple that is coupled to a site-directing molecule, and $R_7$ is H or $OCH_3$. A couple that is coupled to a site-directing molecule may be further described as $O(CH_2CH_2O)_m$- where m is 1–10 and preferably 1–5, or as $O(CH_2)_nCO$- where n is 1–10 and preferably 1–3.

In another preferred texaphyrin A, the substituent $R_1$ is $(CH_2)_2CH_2OH$, $R_2$ and $R_3$ are $CH_2CH_3$, $R_4$ is $CH_3$, $R_7$ is $O(CH_2CH_2O)_2CH_2CH_2OCH_3$, and $R_8$ is a site-directing molecule or a couple that is coupled to a site-directing molecule.

In a further presently preferred texaphyrin A, $R_1$ is $(CH_2)_2CH_2OH$, $R_2$ and $R_3$ are $CH_2CH_3$, $R_4$ is $CH_3$, and $R_7$ and $R_8$ are $O(CH_2CH_2O)_2CH_2CH_2OCH_3$. This texaphyrin is designated "T2BET".

In other presently preferred texaphyrin compounds A, $R_1$-$R_4$, $R_7$, and $R_8$ are as in Table 1 for texaphyrins A1–A22, $R_5$, $R_6$, and $R_9$-$R_{12}$ are H, and M is as defined hereinabove. Most preferred is the compound LuT2BET (compound A2 where M=Lu(III)). While the cited texaphyrins are presently preferred for use in the present invention, the invention is not limited thereto, and any photosensitive texaphyrin may be used.

TABLE 1

Representative Substituents for Texaphyrin Macrocycles of the Present Invention

| TXP | $R_1$ | $R_2$ | $R_3$ | $R_4$ | $R_8$ | $R_7$ |
|---|---|---|---|---|---|---|
| A1 | $CH_2(CH_2)_2OH$ | $CH_2CH_3$ | $CH_2CH_3$ | $CH_3$ | $O(CH_2)_3OH$ | $O(CH_2)_3OH$ |
| A2 | " | " | " | " | $O(CH_2CH_2O)_3CH_3$ | $O(CH_2CH_2O)_3CH_3$ |
| A3 | " | " | " | " | $O(CH_2)_nCON$-linker-site-directing molecule, n = 1–10 | " |
| A4 | " | " | " | " | $O(CH_2)_nCON$-linker-site-directing molecule, n = 1–10 | H |
| A5 | " | " | " | " | $OCH_2CO$-hormone | " |
| A6 | " | " | " | " | $O(CH_2CH_2O)_3CH_3$ | " |
| A7 | " | " | " | " | $OCH_2CON$-linker-site-directing molecule | $O(CH_2CH_2O)_3CH_3$ |
| A8 | " | " | " | " | $OCH_2CO$-hormone | " |
| A9 | " | " | " | " | $O(CH_2CH_2O)_{120}CH_3$ | $O(CH_2CH_2O)_3CH_2$—$CH_2$-N-imidazole |
| A10 | " | " | " | " | saccharide | H |
| A11 | " | " | " | " | $OCH_2CON(CH_2CH_2OH)_2$ | " |
| A12 | " | " | " | " | $CH_2CON(CH_3)CH_2$-$(CHOH)_4CH_2OH$ | " |
| A13 | " | COOH | COOH | " | " | " |
| A14 | " | $COOCH_2CH_3$ | $COOCH_2CH_3$ | " | " | " |
| A15 | $CH_2CH_2CON(CH_2CH_2OH)_2$ | $CH_2CH_3$ | $CH_2CH_3$ | " | " | " |
| A16 | $CH_2CH_2ON(CH_3)CH_2$—$(CHOH)_4CH_2OH$ | " | " | " | $OCH_3$ | $OCH_3$ |
| A17 | $CH_2(CH_2)_2OH$ | " | " | " | $O(CH_2)_nCOOH$, n = 1–10 | H |
| A18 | " | " | " | " | $(CH_2)_n$—CON-linker-site-directing molecule, n = 1–10 | " |
| A19 | " | " | " | " | $YCOCH_2$-linker-site-directing molecule Y=NH, O | " |
| A20 | $CH_2CH_3$ | $CH_3$ | $CH_2CH_2COOH$ | " | $O(CH_2)_2CH_2OH$ | $O(CH_2)_2CH_2OH$ |
| A21 | " | " | $CH_2CH_2CON$-oligo | " | " | " |
| A22 | $CH_2(CH_2)_2OH$ | $CH_2CH_3$ | $CH_2CH_3$ | " | $O(CH_2)_3CO$-histamine | H |

For the above-described uses, texaphyrins are provided as pharmaceutical preparations. A pharmaceutical preparation of a texaphyrin may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining a texaphyrin of the present invention and the pharmaceutically acceptable carriers are then easily administered in a variety of dosage forms. Administration may be intravenous, intraperitoneal, parenteral, intramuscular, subcutaneous, oral, or topical, with topical and intravenous administration being preferred, and intravenous being more preferred.

Solutions of the texaphyrin in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Topical creams, emulsions, solutions, and the like are contemplated for applications to surface areas of the body. Topical application may also be by iontophoresis.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy use with a syringe exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars such as mannitol or dextrose or sodium chloride. A more preferable isotonic agent is a mannitol solution of about 2–8% concentration, and, most preferably, of about 5% concentration. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, permeation enhancers, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Texaphyrins may be incorporated into liposomes for use in the present invention. Liposomes may be prepared by any number of techniques that include freeze-thaw, sonication, chelate dialysis, homogenization, solvent infusion, microemulsification, spontaneous formation, solvent vaporization, reverse phase, French pressure cell technique, or controlled detergent dialysis, for example. Preparation may be carried out in a solution, such as a phosphate buffer solution, containing texaphyrin-lipophilic molecule conjugates so that the conjugate is incorporated into the liposome membrane. Alternatively, the conjugate may be added in already formed liposomes. Liposomes employed in the present invention may be of any one of a variety of sizes, preferably the less than about 100 nm in outside diameter, more preferably less than about 50 nm.

Micelles may be prepared by suspension of a texaphyrin-lipophilic molecule and lipid compound(s) in an organic solvent, evaporation of the solvent, resuspension in an aqueous medium, sonication and then centrifugation. Alternatively, the texaphyrin-lipophilic molecule may be added to preformed micelles.

Techniques and lipids for preparing liposomes and micelles are discussed in U.S. Pat. No. 5,466,438, and references cited therein. The disclosures of each of the foregoing references are incorporated herein by reference.

The texaphyrin to be used in the photodynamic methods of the invention will be administered in a pharmaceutically effective amount. By "pharmaceutically effective" is meant that dose which will, upon exposure to light, provide substantial inhibition of pigmented lesion growth. The specific dose will vary depending on the particular texaphyrin chosen, the dosing regimen to be followed, photoirradiation exposure, and timing of administration. Such dose can be determined without undue experimentation by methods known in the art or as described herein.

In the following examples, PDT of the highly pigmented and metastatic B16 melanoma using LuT2BET resulted in significant tumor retardation and increased longevity of the treated animals. Without being bound by theory, the increased PDT responsiveness of the melanoma may be attributed to the high tumor loading achieved by the texaphyrin in addition to enhanced tissue penetration attained by illumination of the tumor with 732 nm light.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Biodistribution of LuT2BET in Melanoma-Bearing Mice

The present example provides results from a study of the biodistribution of lutetium texaphyrin in melanoma-bearing mice. The biodistribution of LuT2BET was analyzed in C57 mice bearing B16 melanoma at 3 h, 5 h, and 24 h after an intravenous administration of 10 or 20 µmol/kg.

LuT2BET: The synthesis and chemical analysis of lutetium texaphyrin (LuT2BET, texaphyrin A2 of Table 1 where M is lutetium) was provided in U.S. Pat. Nos. 5,252,720 and 5,457,183 and in PCT publication WO 95/10307. LuT2BET was dissolved in 5% mannitol at a 2 mM concentration. LuT2BET absorbs strongly in the far-red region of the electromagnetic spectrum, having a molar extinction coefficient of 23,000 $M^{-1}cm^{-1}$ in this solution at 732 nm, the wavelength used for photoirradiation.

Melanoma Cells: B16F10 melanotic melanoma murine cells were obtained from the University of California, San Francisco Cell Culture Facility. These cells are highly pigmented and metastatic in vivo. Cells were grown in Iscove's Modified Dulbeccos' Medium (Gibco, Grand Island, N.Y.) supplemented with 10% fetal bovine serum (JRH Biosciences, Woodland, Calif.) and penicillin/streptomycin (Sigma, St. Louis, Mo.).

Animals and Tumor Model: Inbred C57BL/6N female mice, (C57 mice) seven to eight weeks of age, were obtained from Simonsen Laboratories Inc. (Gilroy, Calif.). The right flanks of the mice were shaved and depiled the day prior to tumor inoculation. B16F10 cells ($5 \times 10^5$ cells in 0.05 mL PBS) were injected subcutaneously into the right hind flanks. Tumor size, i.e., length (l), width (w), and height (h), was measured 3 times a week with a vernier caliper. Tumor volumes were calculated using the formula for a hemiellipsoid (Rockwell and Kallman, 1972):

$$V = \pi/6 \times (l) \times (w) \times (h)$$

Biodistribution studies were performed on tumors having surface diameters of between about 5.5–7 mm and a depth of 4–6 mm.

Tissue Extraction Procedure: LuT2BET was administered via tail-vein injection at 10 or 20 µmol/kg. Tissues and plasma were analyzed at 3, 5 or 24 h post administration of the photosensitizer. Blood was collected in tubes containing 5 mg of solid EDTA and erythrocytes were removed by centrifugation. Plasma samples (125 µL) were mixed with 10 mM TRITON X-100® and analyzed for texaphyrin content by fluorescence. Weighed tissue samples were frozen in liquid nitrogen, and pulverized using a stainless-steel pulverizer chilled to −40° C. The powdered material was homogenized (POLYTRON®, Brinkman) in 1.6 mL phosphate buffer (50 mM, pH 8.0). These homogenates were then mixed thoroughly with 3.0 mL methanol, and chloroform (3.0 mL) was added. After vigorous shaking on a Thomas Shaking Apparatus (Arthur H. Thomas, Philadelphia, Pa.), the phases were separated by centrifugation (10,000×g, 10 min. room temperature). The chloroform-rich bottom phase was carefully removed and brought to a volume of 3 mL with methanol. Samples were then analyzed for lutetium texaphyrin content by fluorescence (excitation=450 nm. emission=700–800 nm). Recovery of sensitizer was >90%. Sensitizer accumulation is expressed as µg drug/g tissue (wet weight) or per mL plasma.

Statistical analysis: Values are expressed as mean±SD. Values were compared using the unpaired Student's t-test. In the longevity analysis. Kaplan-Meier survival curves and log rank analysis for statistical significance were used. Statistical significance was assumed if $P<0.05$.

The distribution of LuT2BET in tissues and plasma of B16 melanoma bearing C57 mice at 3 h. 5 h, and 24 h following a 10 µmol/kg intravenous injection; and at 5 h, and 24 h following a 20 µmol/kg intravenous injection of the sensitizer is shown in Table 2.

photoirradiated. Photoirradiation of the B16 melanoma 5 h after administration of 10 µmol/kg or 20 µmol/kg LuT2BET produced significant retardation of growth of the tumor; in some cases the longevity of the animals was doubled. PDT response was dependent upon drug dose, irradiation exposure and administration time.

PDT Protocol: C57 mice, bearing B16F10 melanoma as described in Example 1, were used for PDT experiments when the tumors reached surface diameters of between 4–6 mm and a depth of 2.5–3 mm. The mice were injected intravenously with LuT2BET (10 or 20 µmol/kg), and subsequently treated 5 or 24 h later by localized laser irradiation at 732 nm using a LAMBDA PLUS® argon pumped dye laser (Coherent, Palo Alto, Calif.). A 400 µm diameter fiberoptic cable coupled the laser to a microlens which produced uniform light intensity in the treatment field. Light fluences ranged between 150 and 600 J/cm$^2$, and

TABLE 2

Biodistribution of LuT2BET in B16 melanoma-bearing mice

| LuT2BET (µmol/kg) | Time (h) | Plasma | Tumor | Muscle | Liver | Skin |
|---|---|---|---|---|---|---|
| 0 | 0 | 0 | 0 | 0 | 0.32 ± 0.36 | 0 |
| 10 | 3 | 8.93 ± 1.0 | 11.27 ± 3.7 | 1.31 ± 0.4 | 94.52 ± 11.6 | 5.9 ± 1.25 |
| 10 | 5 | 1.22 ± 0.18 | 11.43 ± 1.08 | 0.76 ± 0.15 | 61.91 ± 8.31 | 3.80 ± 1.07 |
| 10 | 24 | 0 | 6.12 ± 1.77 | 0.60 ± 0.16 | 38.65 ± 6.0 | 2.99 ± 0.22 |
| 20 | 5 | 2.65 ± 0.87 | 21.44 ± 10.32 | 1.40 ± 0.48 | 103.80 ± 13.66 | 7.02 ± 0.70 |
| 20 | 24 | 0 | 2.80 ± 0.72 | 1.15 ± 0.48 | 65.91 ± 6.39 | 5.22 ± 1.11 |

The lutetium texaphyrin distribution is expressed as µg/g tissue (wet weight) or µg/mL for plasma. These values represent the mean ± SD of five animals.

The data of Table 2 show that the control group (no photosensitizer) showed only minimal intrinsic fluorescence in the liver; all other tissues were void of material which would fluoresce in the 700–800 nm range after being excited by 450 nm light. Tumor levels of the texaphyrin were higher than plasma, muscle and skin at all three time points. The 20 µmol/kg dose produced greater tissue concentrations compared to the 10 µmol/kg dose, with the exception of the tumor levels at 24 h.

The texaphyrin exhibited good tumor localizing capacity as shown in Table 2. The tumor:muscle ratios, for the 10 µmol/kg dose, were 8.6:1, 15:1, and 10.1:1 for 3 h, 5 h, and 24 h post injection, respectively. The 20 µmol/kg dose yielded ratios of 15.3:1 and 2.4:1, respectively. Some sensitizer was retained in the skin; melanoma to normal skin ratios were between 0.5–3 to 1. High concentrations were found in the liver showing that the texaphyrin is not exclusively retained by the tumor. However, no toxicity was observed in this study.

A comparison with pharmacological data obtained using radiolabeled [$^{14}$C]-LuT2BET in SMT-F bearing mice showed significant but less selectivity. A dose of 8.64 µmol/kg LuT2BET produced drug uptake values of 5.1 µg/g, 4.7 µg/g, and 2.8 µg/g at 3 h, 5 h, and 24 h after injection, yielding tumor:muscle ratios of 8.45:1, 10:1 and 7:1, respectively. Therefore, increased uptake of lutetium texaphyrin into B16 melanoma was observed compared to the mammary carcinoma SMT-F.

EXAMPLE 2

Response to LuT2BET and Photoirradiation in Melanoma-Bearing Mice

The present example provides results of a study wherein melanoma-bearing mice were administered LuT2BET and the power density was set at 150 mW/cm$^2$ as measured with a power meter (Scientech, Boulder, Colo.). The mice were restrained with laboratory tape during photoirradiation.

Tumor Temperature Measurements: Tumor temperature during laser irradiation was monitored with a 33 gauge hypodermic thermocouple probe (Omega Engineering, Stamford, Conn.) placed percutaneously at the base of the tumor.

Results of PDT with LuT2BET in B16F10 melanotic tumors are shown in Tables 3 and 4. No measurable increase in tumor temperature was observed during the course of PDT treatment using light fluences between 150 to 600 J/cm$^2$ at 150 mW/cm$^2$, thereby ruling out hyperthermal effects. Table 3 lists melanoma regrowth with a photosensitive texaphyrin dose of 20 µmol/kg with laser irradiation at 150 or 300 J/cm$^2$ at 5 or 24 h post injection.

TABLE 3

PDT response to 20 µmol/kg LuT2BET in melanoma-bearing mice

| LuT2BET (µmol/kg) | Fluence (J/cm$^2$) | Time[1] (hours) | Regrowth[2] (days) | MST[3] (days) |
|---|---|---|---|---|
| — | — | — | 5.9 ± 1.8, n = 9 | 13, n = 9 |
| — | 400 | — | 6.2 ± 1.6, n = 5 | 16, n = 5 |
| 20 | — | — | 8.2 ± 2.3, n = 5 | 15, n = 5 |
| 20 | 150 | 5h | 10.6 ± 2.9, n = 8 | 26, n = 8 |
| 20 | 300 | 5h | 15.3 ± 2.6, n = 13 | 27, n = 13 |

TABLE 3-continued

PDT response to 20 μmol/kg LuT2BET in melanoma-bearing mice

| LuT2BET (μmol/kg) | Fluence (J/cm$^2$) | Time[1] (hours) | Regrowth[2] (days) | MST[3] (days) |
|---|---|---|---|---|
| 20 | 150 | 24h | 6.7 ± 0.8, n = 7 | 19, n = 7 |
| 20 | 300 | 24h | 9.6 ± 2.1, n = 7 | 20, n = 7 |

[1]Time between sensitizer administration and irradiation. Power density was 150 mW/cm$^2$.
[2]Time to reach ten times the original tumor volume (mean ± SD).
[3]Median survival time following PDT (mean ± SD).

No significant difference in tumor regrowth was seen when comparing normal tumors, those irradiated with 400 J/cm$^2$, and those treated with sensitizer alone. A significant response was seen when the tumors were irradiated 5 h after sensitizer administration (P<0.001). The time for the tumors to regrow (to ten times their original volume) was increased to 15.3 days with a light fluence of 300 J/cm$^2$ compared to 5.9 days for the control group. Irradiation 24 h after photosensitizer injection with a light fluence of 150 J/cm$^2$ did not yield any significant change in tumor regrowth when compared to controls, however an increase in light fluence to 300 J/cm$^2$ increased the time for tumor regrowth to 9.6 days (P=0.002) compared to controls.

Table 4 summarizes PDT responses with administration of 10 μmol/kg LuT2BET.

TABLE 4

PDT response to 10 μmol/kg LuT2BET in B16 melanoma-bearing mice

| LuT2BET (μmol/kg) | Fluence (J/cm$^2$) | Time[1] (hours) | Regrowth[2] (days) | MST[3] (days) |
|---|---|---|---|---|
| — | — | — | 5.9 ± 1.8, n = 9 | 13, n = 9 |
| — | 400 | — | 6.2 ± 1.6, n = 5 | 16, n = 5 |
| 10 | — | — | 7.8 ± 0.8, n = 5 | 17.5, n = 6 |
| 10 | 150 | 3 | 15.0 ± 3.38, n = 12 | 23, n = 3 |
| 10 | 300 | 5 | 8.5 ± 3.0, n = 6 | 17, n = 6 |
| 10 | 400 | 5 | 11.6 ± 2.1, n = 7 | 18.5, n = 8 |
| 10 | 500 | 5 | 13.2 ± 3.5, n = 11 | 23, n = 11 |
| 10 | 600 | 5 | 15.6 ± 3.6, n = 5 | 28, n = 6 |

[1]Time between sensitizer administration and irradiation. Power density was 150 mW/cm$^2$.
[2]Time to reach ten times the original tumor volume (mean ± SD).
[3]Median survival time following PDT.

The effects of progressively greater light doses 5 h after LuT2BET administration (10 μmol/kg) are also shown in Table 4. Following an intravenous injection of 10 μmol/kg and a light fluence of 300 J/cm$^2$, no detectable inhibition of tumor regrowth was seen. However, light doses of 400, 500 and 600 J/cm$^2$ significantly increased the PDT effect of LuT2BET at 10 μmol/kg. At a 600 J/cm$^2$ light dose, the tumors grew to 10× their initial tumor volume in 15.6 days, compared to 5.9 days for untreated controls (P<0.0001).

The B16F10 melanoma line characteristically metastasizes. Tables 3 and 4 show the median survival time (MST) in the 20 and 10 μmol/kg groups, respectively. With regard to both LuT2BET doses, there was no apparent difference between light alone, LuT2BET alone, and the controls. A significant increase in survival time was observed when irradiation was carried out 5 h after the injection of 20 μmol/kg LuT2BET at both 150 and 300 J/cm$^2$; 26 days, P=0.011, and 27 days, P=0.0002, respectively.

A significant increase in survival time after administration of 10 μmol/kg photosensitizer occurred at light fluences of at least about 500 J/cm$^2$; the median survival time of the group treated with 10 μmol/kg sensitizer alone was 17.5 days compared to 23 and 28 days respectively, for 500 and 600 J/cm$^2$.

Thus, LuT2BET proved efficacious in the retardation of the highly pigmented B16 melanoma in C57 mice. Of the two time intervals tested, the most effective time for irradiation was found to be 5 h after LuT2BET administration. When irradiation occurred 24 h after drug administration, a higher light dose was required for a statistically significant therapeutic response. The higher LuT2BET dose of 20 μmol/kg proved more efficacious than the 10 μmol/kg dose using the same irradiation times. A light dose of 300 J/cm$^2$ resulted in regrowth to ten times the original volume in 8.5 days for the 10 μmol/kg group, compared with 15.3 days for the 20 μmol/kg group.

The B16F10 melanoma variant used in this study is highly metastatic (Irimura et al., 1984); the primary cause of death was due to pulmonary metastases. PDT with lutetium texaphyrin significantly increased the survival time of the melanoma-bearing mice.

EXAMPLE 3

Response to LuT2BET and Photoirradiation in Humans with Melanoma

A patient with recurrent melanoma received a single dose of LuT2BET (0.5 μmol/kg; 2 mM in 5% mannitol/water; (a human equivalent of 10% of the mouse $LD_{50}$)), administered intravenously, followed three hours later by photoirradiation by laser (732 nm light, 150 J/cm$^2$ at a power density of 75 mW/cm$^2$ using a LAMBDA PLUS® laser, Coherent, Palo Alto, Calif.). Four fields and a total of ten individual lesions were treated. Slight edema and erythema were noted at the treatment sites following the light irradiation. Several days post-therapy, several of the smaller lesions had disappeared, several of the larger lesions had decreased in size, and the remaining lesions showed no change. The patient exhibited no skin phototoxicity. At two months post-therapy, the patient's lesions continued to show improvement.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Andreoni, A., et al., (1991) *Cancer Lett.*, 61, 89–94.
Bielec, J., et al., (1986) *J Chem. Soc. Faraday Trans.* II, 82, 1469–1474.
Biolo, R., (1994) *Photochem. Photobiol.* 59, 362–365.
Brown, S. B. and T. G. Truscott., (1993), *Chemistry in Britain*, 955–958.
Chen, Y. T. et al., (1995) *Proc. Natl. Acad. Sci.* 92, 8125–8129.
Dougherty, T. J., (1981) *J. Invest. Dermatol.*, 77, 122–124.
Gomer, C. J., et al., (1987) *Br J. Cancer*, 56, 27–32.
Grossweiner, L. I., (1991) *Lasers, Surg. Med.*, 11:165–173.
Haylett, A. K., et al., (1995) *Cancer Lett.*, 88, 191–199.
Henderson, B. W., and T. J. Dougherty (1992) *Photochem. Photobiol.* 55, 145–157.
Irimura, T., and G. L. Nicolson (1984) *Cancer Res.*, 44, 791–798.
Kreimer-Birnbaum, M. (1989) *Semin. Hematol.* 26, 157–173.
Lim, H. W., et al., (1985) *J. Invest. Derm.*, 84, 114.
MacRobert, A. J., et al., (1989) What are the ideal photoproperties for a sensitizer? In:
*Photosensitizing Compounds: Their Chemistry, Biology and Clinical Use.* (Edited by G. Bock and S. Harnett), Ciba Foundation Symposium 146, pp. 4–16 Wiley, Chichester.
Moan, J. and K. Berg, (1992), *Photochem. Photobiol.*, 55:931–948.
Nelson, J. S., et al., (1988) *J. Natl Cancer Inst.*, 80, 56–60.
Pass, H. I. (1993) *J. Natl Cancer Inst.* 85, 443–456.
Rockwell, S. and R. F. Kallman (1972) *Cell Tissue Kinet.*, 5, 449–457.
Schwechheimer, K. and L. Zhou (1995) *Virchows Archiv.*, 426, 351–353.
Sealey, R. C., et al., (1984) *Photochem. Photobiol.*, 40, 453–459.
Sessler, J. L., et al., (1994) *Acc. Chem. Res.* 27, 43–50.
Sindelar et al, (1991) *Arch. Surg.*, 126:318–324.
Young, S. W., et al., (1994) *Invest. Rad.* 29, 330–338.

What is claimed is:

1. A method for photodynamic therapy of a pigmented lesion or of a lesion obscured by melanodermic tissue of a subject, comprising:

administering a photosensitive texaphyrin to the subject; and photoirradiating the lesion.

2. The method of claim 1 wherein the pigmented lesion is a melanodermic lesion.

3. The method of claim 2 wherein the melanodermic lesion is a neoplasm or a malignant lesion.

4. The method of claim 3 wherein the malignant lesion is melanoma.

5. A method for photodynamic therapy of a pigmented lesion or of a lesion obscured by melanodermic tissue of a subject, comprising:

administering a photosensitive texaphyrin having structure A to the subject; and photoirradiating the lesion:

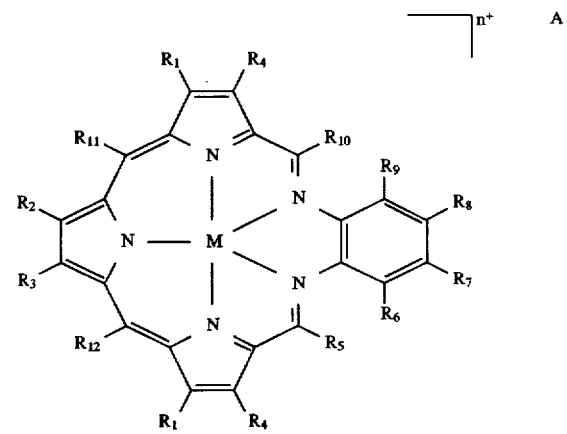

wherein

M is H or a diamagnetic metal cation;

$R_1$–$R_4$, $R_7$ and $R_8$ are independently hydrogen, halide, hydroxyl, alkyl, aryl, haloalkyl, nitro, formyl, acyl, hydroxyalkyl, alkoxy, hydroxyalkoxy, saccharide, carboxy, carboxyalkyl, carboxyamidealkyl, a site-directing molecule, or a couple that is coupled to a site-directing molecule;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, aryl, hydroxyalkyl, alkoxy, hydroxyalkoxy, carboxyalkyl, carboxyamidealkyl or a couple that is coupled to a saccharide, or to a site-directing molecule; and n is an integer less than or equal to 5.

6. A method for photodynamic therapy of melanoma of a subject, comprising:

administering a photosensitive texaphyrin having structure A to the subject; and photoirradiating the melanoma:

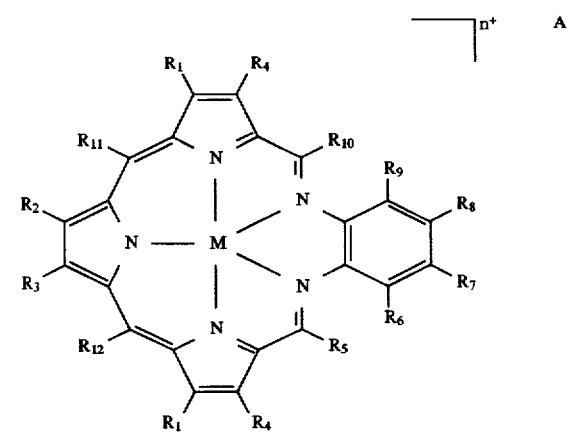

wherein

M is a diamagnetic metal cation;

$R_1$–$R_4$, $R_7$ and $R_8$ are independently hydrogen, halide, hydroxyl, alkyl, aryl, haloalkyl, nitro, formyl, acyl, hydroxyalkyl, alkoxy, hydroxyalkoxy, saccharide, carboxy, carboxyalkyl, carboxyamidealkyl, a site-directing molecule, or a couple that is coupled to a site-directing molecule;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, aryl, hydroxyalkyl, alkoxy, hydroxyalkoxy, carboxyalkyl, carboxyamidealkyl or a couple that is coupled to a saccharide, or to a site-directing molecule; and n is an integer less than or equal to 5.

7. A method for inhibiting metastasis of melanoma in a subject, comprising administering a photosensitive texaphyrin having structure A to the subject; and photoirradiating the subject:

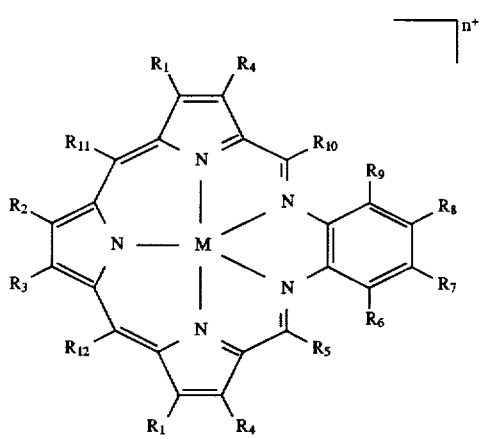

A wherein

M is a diamagnetic metal cation;

$R_1$–$R_4$, $R_7$ and $R_8$ are independently hydrogen, halide, hydroxyl, alkyl, aryl, haloalkyl, nitro, formyl, acyl, hydroxyalkyl, alkoxy, hydroxyalkoxy, saccharide, carboxy, carboxyalkyl, carboxyamidealkyl, a site-directing molecule, or a couple that is coupled to a site-directing molecule;

$R_6$ and $R_9$ are independently selected from the groups of $R_1$–$R_4$, $R_7$ and $R_8$, with the proviso that the halide is other than iodide and the haloalkyl is other than iodoalkyl;

$R_5$ and $R_{10}$–$R_{12}$ are independently hydrogen, alkyl, aryl, hydroxyalkyl, alkoxy, hydroxyalkoxy, carboxyalkyl, carboxyamidealkyl or a couple that is coupled to a saccharide, or to a site-directing molecule; and n is an integer less than or equal to 5.

8. The method of claim 5, 6, or 7 wherein the site-directing molecule is an antibody having binding specificity for tyrosinase.

9. A method for photodynamic therapy of melanoma of a subject, comprising:

administering a photosensitive texaphyrin to the subject; and photoirradiating the melanoma.

10. A method for inhibiting metastasis of melanoma in a subject, comprising administering a photosensitive texaphyrin to the subject; and photoirradiating the subject.

11. The method of claim 1, 9, or 10 wherein the photosensitive texaphyrin is selected from the group consisting of texaphyrins A1–A22 of Table 1.

12. The method of claim 1, 9, or 10 wherein the photosensitive texaphyrin is bound to a diamagnetic metal cation and the diamagnetic metal cation is Lu(II), La(III), In(III), Y(III), Dy(III), Zn(II) or Cd(II).

13. The method of claim 1, 9, or 10 wherein the photosensitive texaphyrin is bound to a diamagnetic metal cation and the diamagnetic metal cation is Lu(III).

14. A method for photodynamic therapy of melanoma of a subject, comprising:

administering LuT2BET to the subject; and photoirradiating the melanoma.

15. The method of claim 1, 9, 14, 10, 6, or 7 wherein the photoirradiating is with light having a wavelength range of about 700 to about 900 nanometers.

16. The method of claim 1, 9, 14, 10, 6, or 7 wherein the photoirradiating is with light having a wavelength range of about 730 to about 770 nanometers.

17. The method of claim 1, 9, 14, 10, 6, or 7 further comprising the steps of administering a second texaphyrin having paramagnetic properties to the subject, and imaging the subject.

18. The method of claim 1, 9, 14, 10, 6, or 7 further comprising the step of administering ionizing or particulate radiation to the subject.

19. The method of claim 9, 14, 10, 6, or 7 where the melanoma is amelanotic melanoma.

20. The method of claim 1, 9, or 10 wherein the photosensitive texaphyrin is LuT2BET.

21. The method of claim 1, 9, or 10 wherein the photosensitive texaphyrin has a methyl group attached to a ring nitrogen.

22. A method for photodynamic therapy of a pigmented lesion or of a lesion obscured by melanodermic tissue of a subject, comprising:

administering LuT2BET to the subject; and photoirradiating the lesion.

23. A method for photodynamic therapy of a pigmented lesion or of a lesion obscured by melanodermic tissue of a subject, comprising:

administering a texaphyrin selected from the group consisting of texaphyrins A1–A22 of Table 1 to the subject; and photoirradiating the lesion.

24. The method of claim 6 or 7 wherein the diamagnetic metal cation is Lu(III), La(III), In(III), Y(III), Dy(III), Zn(II) or Cd(II).

25. The method of claim 6 or 7 wherein the diamagnetic metal cation is Lu(III).

26. A method for inhibiting metastasis of melanoma in a subject, comprising administering LuT2BET to the subject; and photoirradiating the subject.

* * * * *

UNITED STATES PATENT AND TRADEMARK OFFICE
CERTIFICATE OF CORRECTION

PATENT NO.:   5,775,339

DATED:   July 7, 1998

INVENTOR:   Woodburn, *et al.*

It is certified that errors appear in the above-identified patent and that said Letters Patent is hereby corrected as shown below:

At Claim 12, column 22, line 6, delete "(II)", and substitute -- (III) --, therefor.

Signed and Sealed this

Twenty-ninth Day of September, 1998

Attest:

BRUCE LEHMAN

*Attesting Officer*   *Commissioner of Patents and Trademarks*